United States Patent

Alla et al.

[11] Patent Number: 6,035,853
[45] Date of Patent: Mar. 14, 2000

[54] FEMALE CONDOM

[76] Inventors: Ravikumar Alla; Madhusudhan Alla; Raghunatha Alla, all of 9 Webster Ct., Plainsboro, N.J. 08536

[21] Appl. No.: 08/853,030

[22] Filed: May 8, 1997

Related U.S. Application Data

[63] Continuation-in-part of application No. 08/853,030, May 8, 1997
[60] Provisional application No. 60/035,546, Dec. 31, 1996.

[51] Int. Cl.[7] ........................................ A61F 6/06

[52] U.S. Cl. ........................ 128/830; 128/844; 128/918

[58] Field of Search .................... 128/842, 844, 128/918; 604/347–353

[56] References Cited

U.S. PATENT DOCUMENTS

| | | | |
|---|---|---|---|
| 5,163,448 | 11/1992 | Foldesy | 128/844 |
| 5,209,241 | 5/1993 | Hardy | 128/844 |
| 5,325,871 | 7/1994 | Reddy | 128/844 |
| 5,638,829 | 6/1997 | Najor | 128/844 |

*Primary Examiner*—Michael A. Brown
*Attorney, Agent, or Firm*—Reising, Ethington, Learman & McCulloch PLLC

[57] ABSTRACT

A female condom has a pouch that has a predeployment position on the outer surface of a shield portion wherein the pouch includes a telescoped portion forming an exteriorly accessible pocket for receiving a retention sponge; the retention sponge is sealed within the exteriorly accessible pocket by a removable cover that seals the sponge within the exteriorly accessible pocket while in its predeployment position; the locking and sealing member is removable from the telescoped pouch portion for deployment.

33 Claims, 10 Drawing Sheets

FEMALE CONDOM

This application is a continuation-in-part of U.S. Ser. No. 08/853,030 filed May 8, 1997 that is a continuation in part of provisional application 60/035,546 filed Dec. 31, 1996.

FIELD OF THE INVENTION

This invention relates to prophylactic devices and more particularly to female condoms having a pouch portion insertable into a deployed position.

BACKGROUND OF THE INVENTION

With the widespread prevalence of venereal disease and the growing occurrence of AIDS (acquired immune deficiency syndrome), there is an increasing need for effective means to prevent the transmission of such diseases through sexual contact and resultant exchange of bodily fluids between a user and the user's partner.

Heretofore, conventional means for preventing the transmission of such bodily fluids and exposure to such diseases because of bodily contact have included the use of condoms, jells, creams and the like.

Additionally, there have been proposals to provide female prophylactic devices, which can be worn by a female prior to use and disposed of following use. While such conventional and proposed devices are suitable for their intended purpose, it has been found that they are not totally effective for various reasons.

One example of a prior prophylactic device for use by females is that set forth in U.S. Pat. No. 3,536,066. The '066 patent shows a pant styled garment having a bellow configured pouch thereon which is located on the exterior of the pant. The bellows is preinsertable into the vaginal canal of a female prior to use. After the bellows is inserted, convolutions therein are extended to provide for extension of the bellows to accommodate an erected penis during use of the contraceptive device. The device requires preinsertion of a segment of the bellows and does not include means for piloting a large pouch-like member into a vaginal canal or means for holding such a member in place. Furthermore, the garment portions of the device are formed from rubber material which is configured to contact a large portion of the waist region of the user as well as the buttocks and hip regions of a user so as to cause possible irritation and discomfort when worn for substantial periods of time prior to use.

U.S. Pat. Des. No. 254,809 to Meldahl discloses a device for use as a male contraceptive. While the contraceptive has a larger diameter than typical condoms, it does not include a portion thereon which will serve as the device to prevent the passage of bodily fluids between a user and a partner. There are not straps to hold the device in place.

Swiss Patentschrift No. 117,234 (1925) discloses a female contraceptive device having a pouch that includes a generally circular collar on the other end thereof. There is no suggestion to provide a portion of the device that will cover and conform to the full perineum region of a user. Furthermore, there is no suggestion of how to hold the device in place during use. Furthermore, the outer lip or collar of the condom can enter the vagina during intercourse so as to cause undesirable exposure of the users to the other's bodily fluids.

U.S. Pat. No. 4,735,621 likewise shows a thin walled, condomlike, tubular protective device for insertion into a vaginal canal. It includes a resilient ring on one end thereof to anchor the device in the vaginal canal.

The retention ring of the '621 patent is an integral part of the condom which requires special manufacturing tooling. Furthermore, the retention ring is configured to have a diameter corresponding to that of the pouch and a cross-sectional diameter that is small compared to the diameter of the ring. As a consequence the ring requires careful placement within the vagina so as to assure that it will fit in an interference relationship therewith to prevent the pouch from being withdrawn during coitus. Furthermore, the '621 retention ring may be oriented in a direction that will produce undesirable contact with an erected penis, i.e., causing pain during intercourse. Furthermore, the outer ring goes into the vagina during intercourse causing undesirable exposure of the users to bodily fluids.

Other female condoms have been proposed that include an internally located resilient insert element for holding the pouch portion of the female condom in place. One example is set forth in PCT International Publication No. WO90/00038 wherein an insert can be directed into the closed end of the pouch portion of the female condom. In this application, the insert is an absorbent and flexible expanded plastic material that includes spermicides or antiviral agents. The female condom in this case requires the use of a special insert and an applicator for performing the deployment of the female condom into its deployed position within a user.

Another example of a female condom having an interiorly located retainer element is set forth in U.S. Pat. No. 5,325,871 that discloses the use of an insertable retention member that can be compressed during insertion and that will, following deployment of the female condom into its deployed position, serve both as a radially outwardly directed retention pressure device as well as a device for dispensing spermicides, fungicides or the like.

While suitable for their intended purposes, such aforesaid devices have been found to lack an ease of application that will make the female condom acceptable and convenient to most users.

Figure 1:
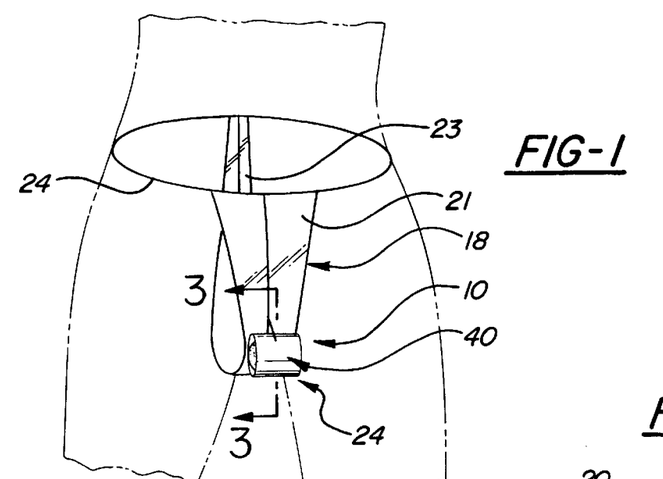
FIG. 1 is a front elevational view of the a first embodiment of the present invention in its predeployment position.
Figure 2:
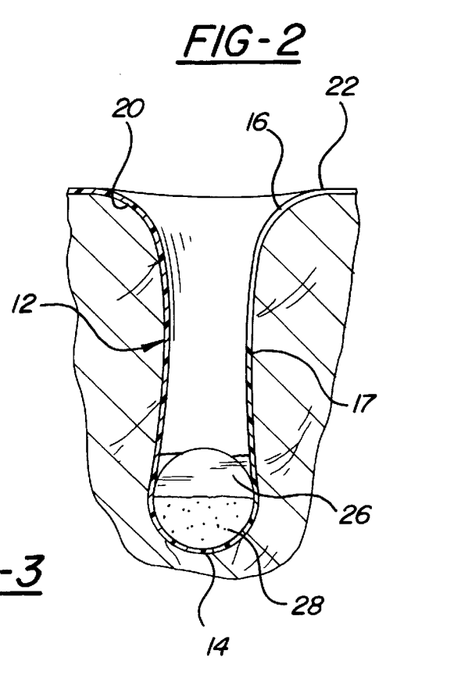
FIG. 2 is a fragmentary view of the embodiment in FIG. 1, shown in its deployed position.

A counterpart to PCT No. WO/00038 is U.S. Pat. No. 5,193,555. As shown in FIG. 1 this invention requires use of an insertion tool 15. Another female condom requiring an insertion tool is shown in U.S. Pat. No. 5,146,930. In the '555 patent retention is provided by a multi-fingered insert with a central portion and a radially outwardly directed portion that springs out following tool insertion for holding the condom pouch in place. In the '930 patent retention is provided by a series of flexible protrusions that are on the outside of the pouch and that are inclined in a direction to prevent pull-out of the pouch. In both the '555 and '930 patent the pouch is connected to a shield that is arranged around the opening to the pouch and the pouch opening is located generally centrally of a thicker shield having an enlarged portion that holds the pouch opening centered while covering the entrance to the vagina.

While such condoms provide protection and cover the perineum of a user they are difficult to insert into the user and are uncomfortable if kept in place during walking and the like since the outer thicker shield is continuously spread open to keep the pouch opening centered with respect to the shield surface. All of the above condoms reduce pleasure to one or both partners during intercourse.

Accordingly, another feature of the present invention is to provide an easily inserted female condom that includes a pouch that has an extension thereon having the same wall thickness as the pouch and is configured to laterally collapse and expand freely to accommodate user movements. The arrangement does not require a separate thicker shield member arranged in a spread position to center the pouch opening with respect to the shield.

In the embodiment of FIG. 1, the shield portion is formed of the same wall thickness as that of the pouch and is arranged to easily collapse laterally. As a consequence, once inserted in place, the shield will, because of a thin wall having a thickness range of 0.02 mm to 0.06 mm, will enable the front and rear walls to easily move laterally to accommodate user movement.

Still another problem with female condoms is the fact that they can interfere with pleasurable coitus. Thus, in accordance with another aspect of the invention sponge fillers are provided on the pouch on either side thereof closely adjacent the shield for filling any gaps between the vaginal wall and to form a tight opening for penal insertion in the vicinity of the clitoris for providing stimulation to both male and female users of the female condom.

Still another problem with female condoms is that of accidental withdrawal and leakage from the female condom. Thus, in accordance with still another aspect of the present invention, a second premolded thin member is heat sealed to a shield on the open end of the female condom to provide a labyrinth seal against leakage from the interior of the female condom and to provide a directional guide into the interior of the female condom while providing an extension on the end of the female condom that will deploy automatically to prevent inadvertent withdrawal.

SUMMARY OF THE PRESENT INVENTION

In the present invention, a female condom has a pouch with a predeployment and a deployment position with respect to the inner and outer surface of a shield portion that enables the pouch of the female condom to be initially placed on a user such that the shield portion will cover the perineum region of the user. A retention sponge is located within an exteriorly accessible pocket of the pouch and the exteriorly accessible pocket and is held in place therein by member that is bonded to the inner surface of the pouch adjacent its closed end; the retention member holds the sponge in its predeployment position in a telescoped part of the pouch that is accessible from the exterior of the female condom to provide for insertion of the sponge and unfolding of the pouch into a fully interiorly located deployed position in which the sponge will force against the inner surface of the pouch adjacent its closed end to hold the closed end against the vagina walls and thus hold the pouch fully extended within the vagina in its deployed position.

In another aspect of the invention, the shield is an extension on the open end of the pouch that is of the same wall thickness as the pouch and is open on at least part of its periphery to provide lateral flexibility that will adjustably conform the shape of the shield to the perineum attached to a V shaped rim with anterior, posterior angle and has the characteristics of a spring mechanism when the female condom is in its deployed position for providing greater comfort on the user during walking, sitting and other changes in user position.

In accordance with another aspect of the present invention, the pouch of the female condom of the present invention includes a retention strap bonded to the inside surface of the pouch adjacent its closed end into which the sponge is located during initial assembly and thereafter located with respect to telescoped outer wall portions of the pouch that forms the exteriorly accessible pocket therein. The retention strap also covers the sponge so that the glans penis will not rub against the sponge in a manner that can cause irritation.

In another aspect of the invention the retention sponge and telescoped pouch is covered by a locking and sealing member when the telescoped pouch is in its predeployment position. The locking and sealing member will prevent lubricant in the telescoped pouch from leaking out into the outer package and also keeping the lubricant in its original position during intercourse so that there will be enough lubricant for bother partners during intercourse. The locking and sealing member is configured to be easily removable from the exteriorly accessible pocket and the user thereafter is able to insert the pouch, along with the sponge, into a fully deployed position within the user in a manner that will prevent easy pull-out of the pouch from the deployed position.

In one embodiment of the invention, the exteriorly accessible pocket is sealed by a locking and sealing member having a cover that is removably connected to the pouch. The cover can include a ring, patch or sleeve configuration or equivalents thereof as long as the exteriorly accessible pocket is completely closed by the locking and sealing member when in place on the pouch.

In all embodiments, the locking and sealing member is located on the outer surface of the shield portion so as to be readily removable from the female condom when the shield portion is securely in place over the perineum.

The telescoped outer wall portions of the pouch that form the exteriorly accessible pocket are positioned for insertion into a deployed position wherein the sponge is concurrently placed, with the closed end of the female condom, into a fully deployed position within the user such that it will be securely connected against pull-out during intercourse.

Accordingly, one feature of the present invention is to provide a female condom having a pouch thereon with a rolled up predeployment position on the outer surface portion of a shield portion; the pouch also having a deployed position on the inner surface portion thereof; the pouch including telescoped outer wall portions in its predeployment position defining an exteriorly accessible pocket having a retention sponge therein.

Another feature of the present invention is a locking and sealing member that covers the exteriorly accessible pocket for controlling fluid leakage into an outer package; the locking and sealing member including a segment connected to the pouch adjacent the open end thereof for locking the telescoped outer wall portions in a predeployment position and wherein the locking and sealing member is easily removable for enabling the pouch to be place in its deployed position.

A further characterization of the invention is that the retention sponge is located within a telescoped pocket that is covered in part by a cover that is removably connected to the pouch of the female condom.

Still another characterization of the present invention is that the locking and sealing member includes an opening therein through which the shield portion of the female condom extends outwardly from the pouch for clamping the shield portion prior to deployment.

Still another object of the present invention is to provide a locking and sealing member cover in the form of a ring having an opening therein through which the shield portion extends into overlying relationship with the perineum of a user prior to deployment of the female condom into its deployed position.

Still another object is to provide such a locking and sealing member in the form of a ring that includes first and second ends that are joined together adjacent the outer surface of the shield portion and in proximity of the open end of the pouch of a female condom.

Still another object of the present invention is to further seal a locking and sealing member having such an opening therein by the provision of foldable sides on the locking and sealing member that are positionable following insertion of the shield portion through the locking and sealing member to overlie the opening to prevent leaking therethrough into the interior of the locking and sealing member.

Yet another characterization of the present invention is that it can include a strap portion across the width of the closed end of the pouch for insertion of a resilient retention sponge prior to forming telescoped outer wall portions on the pouch having an exteriorly accessible pocket that is sealed.

Yet another characterization of the present invention is that it can include a strap portion formed as a closed pouch across the width of the closed end of the pouch for insertion of a resilient retention sponge prior to forming telescoped outer wall portions on the pouch having an exteriorly accessible pocket.

Yet another characterization of the present invention is that it can include a strap portion formed as a pouch having laterally opened ends and extending across the width of the closed end of the pouch for insertion of a resilient retention sponge prior to forming telescoped outer wall portions on the pouch having an exteriorly accessible pocket.

Still another feature of the present invention is the provision of sponge members therein serving as cavity fillers adjacent the shield portion of the female condom.

Yet another feature of the present invention is the provision of an extendable shield on the entrance end of a female condom for protecting against leakage from the interior of a pouch and for protecting against inadvertent withdrawal during coitus.

Yet another feature of the present invention is to incorporate a semi-hard piece of material in or over the pouch near the clitoris in deployment position for stimulation of the clitoris during intercourse.

DESCRIPTION OF THE DRAWINGS

Other advantages, features and objects of the present invention will become more apparent from the following detailed description when taken in conjunction with the appended drawings wherein.

DETAILED DESCRIPTION OF PREFERRED EMBODIMENTS OF THE PRESENT INVENTION

Referring now to FIG. 1, a female condom 10 is shown in a predeployment position on a user. The female condom 10 has a pouch 12 with a closed end 14 and an open end 16. A tubular outer wall 17 joins the closed end 14 with the open end 16. A shield portion 18 has an inner surface 20 and an outer surface 22 and comprises a front panel 21 and a rear panel 23 for covering waistband 24 that is made of a suitable resilient material and is configured to fit on the hips of a user.

Figure 3:
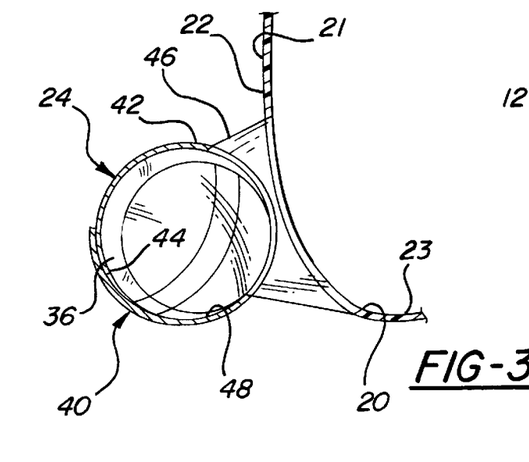
FIG. 3 is a sectional view taken along the line 3—3 of FIG. 1 looking in the direction of the arrows and showing a shield portion opening and retention tab segments of a locking and sealing member.

In accordance with one aspect of the present invention, the pouch 12 is preconfigured to have a rolled up predeployment position shown at 24 in FIGS. 1 and 3. The predeployment position includes a predeployment telescoped portion 30 shown in FIG. 4. The predeployment position locates the pouch on the outer surface 22 of the front panel 21 in a position that will enable the female condom to be easily positioned on the user by steps to be disclosed, while retaining the pouch portion in a location for easy deployment from a predeployment position into a deployed position within the vaginal tract of a user.

Figure 5:
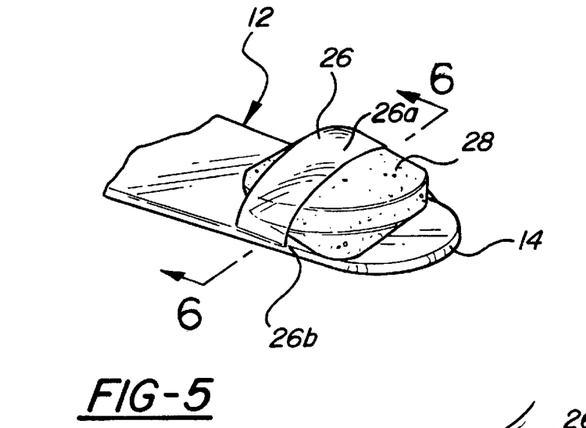
FIG. 5 is a fragmentary elevational view showing a strap for connecting a retention sponge on the end of a pouch portion of the present invention prior to the predeployment position.
Figure 6:
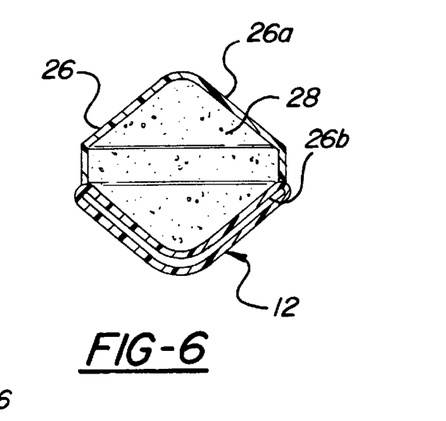
FIG. 6 is a sectional view taken along the line 6—6 of FIG. 5 looking in the direction of the arrows.
Figure 7:
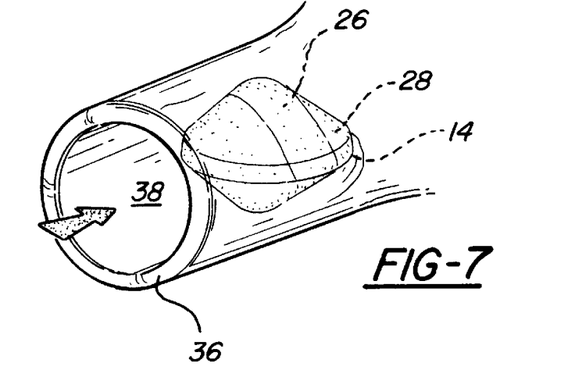
FIG. 7 is an enlarged fragmentary view showing a resilient retention sponge in FIGS. 5 and 6 located in telescoped outer walls of a pouch forming an exteriorly accessible pocket prior to sealing thereof by a locking and sealing member as shown in FIGS. 3 and 4.

More specifically, as shown in FIG. 5, to accomplish this objective, the pouch 12 has a sponge retention strap 26 thereon connected across the width of the closed end 14 thereof. The strap 26 has a semicircular configuration and is two walled at 26a, 26b to form an umbrella like cover as shown in FIG. 6 to enclose the outer surface of a resilient retention sponge 28 between the end 14 and the strap 26. The strap 26 thus covers the sponge 28 during use so that there is no direct contact between a penis and the sponge and will prevent lubrication in the pouch being absorbed by the sponge.

In accordance with the present invention, the sponge member and pouch 12 are located in a predeployment position on the outer surface 22 of the front panel 21 of the shield portion 18 to be readily accessible to a user for deployment as will be described. In the predeployment position, the tubular outer wall 17 has a telescoped portion 30 formed by wall segments 32 and 34 of the pouch 12. The wall segment 32 extends from the closed end 14 and is connected to the wall segment 34 by a rolled segment 36. Together the telescoped portion 30 forms an exteriorly accessible pocket 38. Once formed to have the telescoped portion 30, the pouch 12 is sealed by a locking and sealing member 40 best shown in FIGS. 1 and 3. In this embodiment, the locking and sealing member 40 has a ring configuration with opposite ends 42, 44 thereon that are secured together. An opening 46 in the locking and sealing member 40 is arranged so that the front and rear panels 21, 23 are easily positioned on a user as shown in FIG. 1. Further, the locking and sealing member 40 locates the sponge 28 in a sealed relationship on the front of the user in a predeployment position that is easily accessible for positioning in a deployed location.

More specifically, the inner surface 48 of the locking and sealing member 40 will cover and seal the exteriorly accessible pocket 38 as best shown in FIG. 3. The rolled segment 36 is folded upon itself and the locking and sealing member 40 will control leakage of fluid that might be present within the sponge member 28 prior to deployment.

Figures 14A, 14B, 14C, 14D:
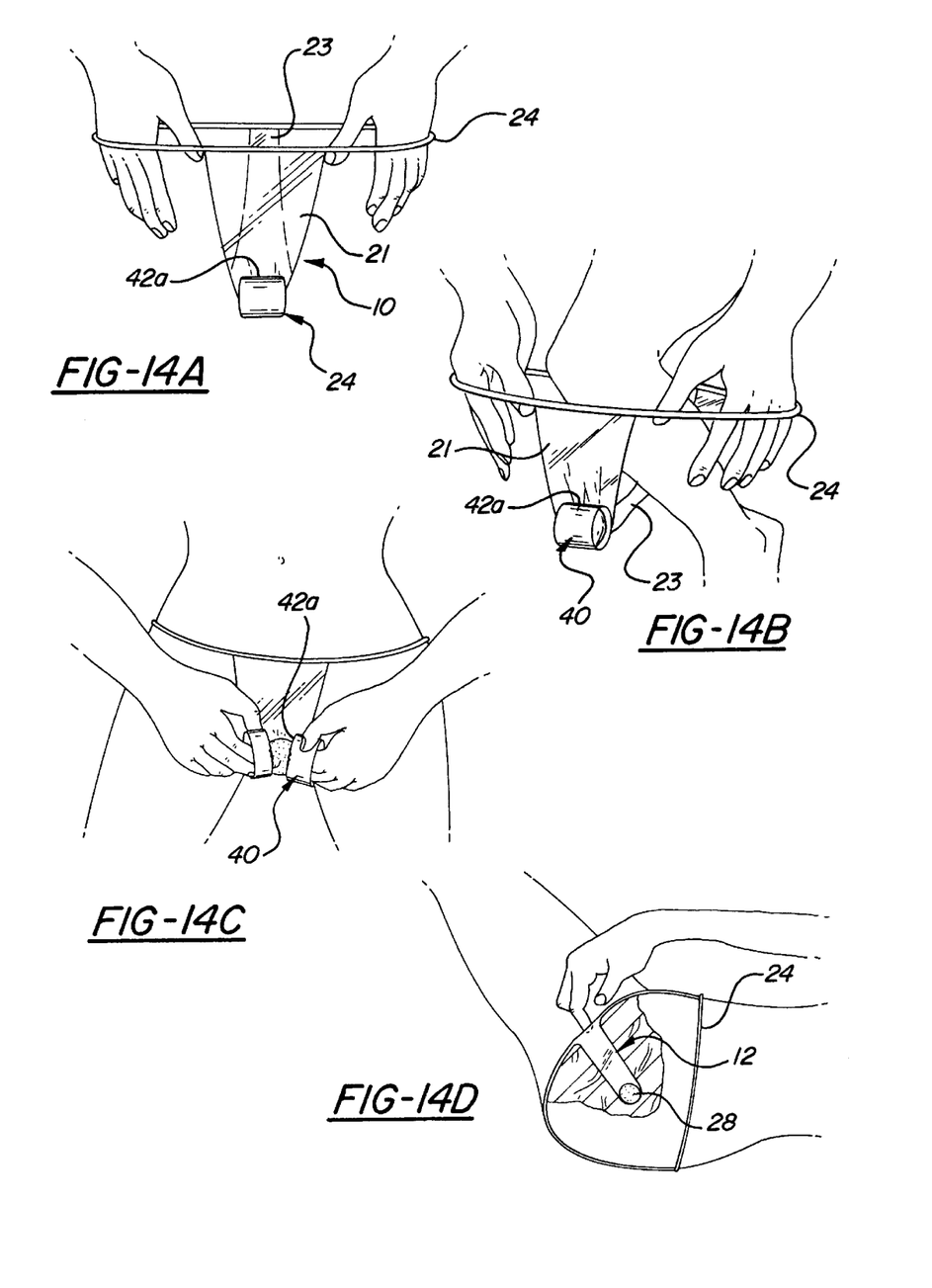
FIGS. 14A–14D are diagrammatic views of a method for deployment of the present invention.

The manner in which the embodiment of FIGS. 1–4 is located on a user and then positioned between its predeployment position and its deployment position is shown in FIGS. 14A–14D. As shown in FIG. 14A, the female condom 10 is gently unfolded from a package and hands of the user are placed in the waistband 24 so that it can be expanded while the palms of the hands face inwardly. This stretches the waistband 24 so that it is easy to step into the female condom (FIG. 14B). In this embodiment, the locking and sealing member 40 is positioned at a point where it can be removed easily at a notch 42a therein that captures both sides of the front panel 21 where it exits the opening 46. The locking and sealing member 40 is thus easily torn from the female condom such that the exteriorly accessible pocket 38 of predeployment telescoped position is open (FIG. 14C). Thereafter, the pouch 12 can be inserted into a deployed position (FIG. 14D) along with sponge 28 deeply into the user so that the sponge 28, when expanded, will prevent pullout of the pouch during intercourse. While a split ring member 40 is shown, a continuous ring with an opening 46 also would serve as a locking and sealing member.

Figure 8:
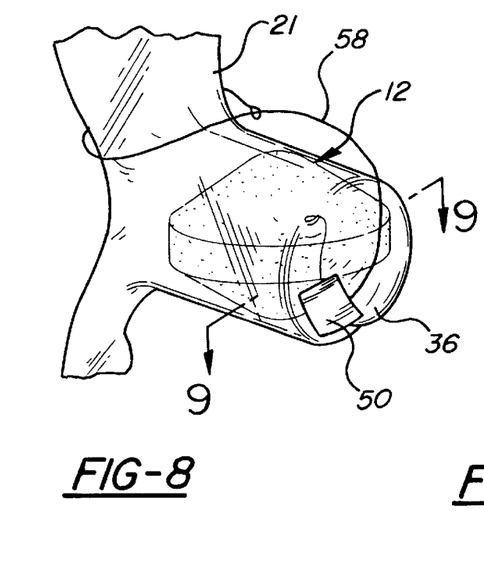
FIG. 8 is a front elevational view of a second embodiment of the present invention in a predeployment position.
Figure 9:
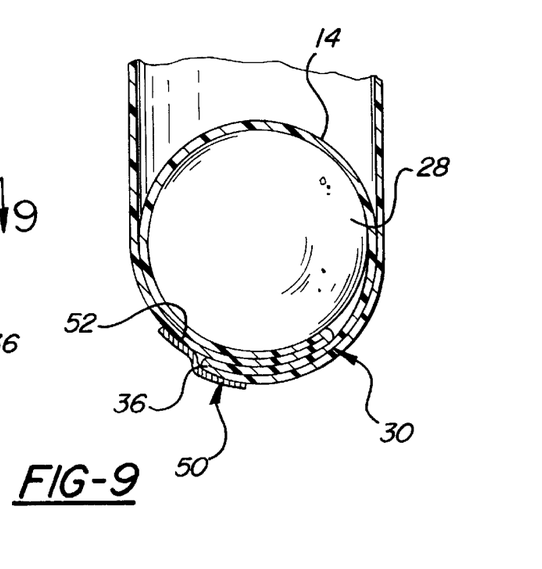
FIG. 9 is an enlarged fragmentary cross sectional view of the locking and sealing member taken along the line 9—9 in FIG. 8 looking in the direction of the arrows.

In the embodiments of FIGS. 8 and 9, a locking and sealing member 48 includes a cover 50 that overlies the folded, rolled segment 36 of the pouch 12, as best shown in FIG. 9. The cover 50 has a patch configuration and includes a suitable adhesive 52 on the interior surface thereof that will hold the rolled segment 36 closed when the female condom is in its deployed position. The cover 50 is locked in place by a string 53 that ties around the front panel 21 and is easily removed for providing access to the exteriorly accessible pocket 30. Thereafter, the female condom of this embodiment is deployed in the same fashion as set forth above.

Figure 10:
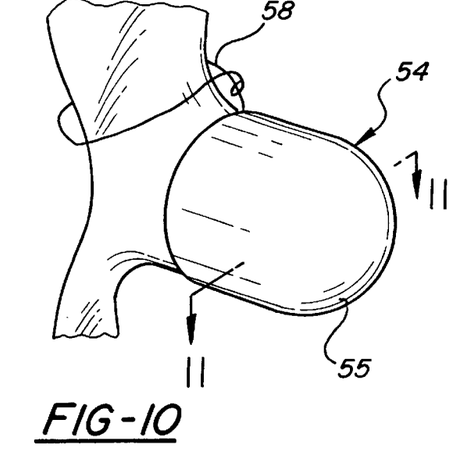
FIG. 10 is a front elevational view of another embodiment of the present invention shown in its predeployment position.
Figure 11:
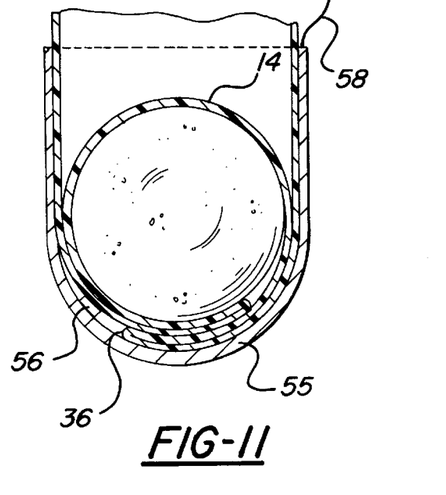
FIG. 11 is an enlarged fragmentary cross-sectional view of the locking and sealing member taken along the line 11—11 in FIG. 10 looking in the direction of the arrows.

In a still further embodiment of the invention shown in FIGS. 10 and 11, a locking and sealing member 54 includes a cover 55 formed as a sock that fits over the rolled segment 36. In this embodiment, the cover 55 has a press fit sealing relationship with the pouch or it can include adhesive segments 56 thereon for securing the cover 55 in a sealed relationship with respect to the pouch when in its predeployment position. If desired, tie strings 58 are secured to cover 55 to lock the cover 55 in place on the shield.

Figure 4:
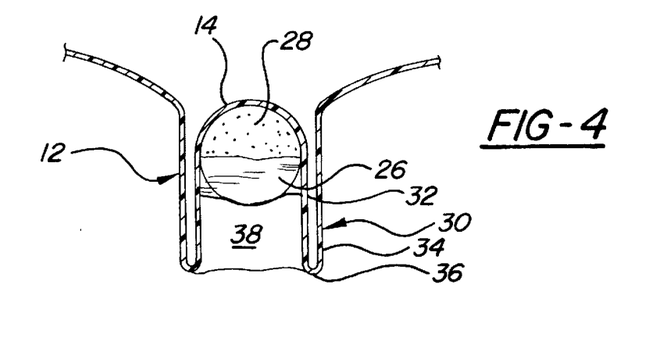
FIG. 4 is a sectional view following removal of the locking and sealing member.
Figure 12:
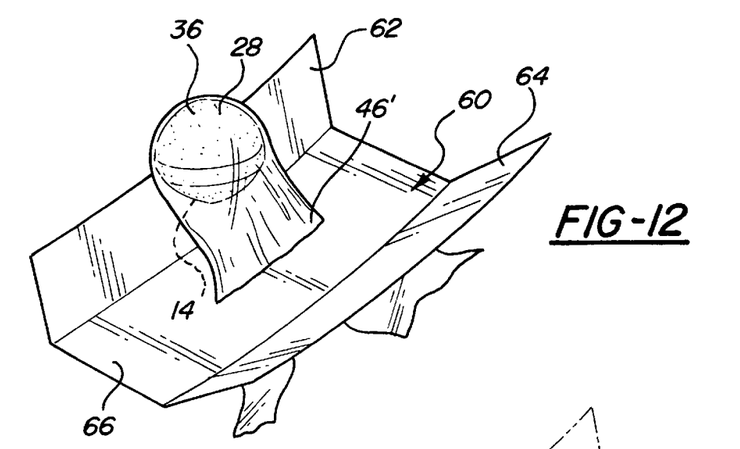
FIG. 12 is a perspective view of another embodiment of a locking and sealing member in a partially assembled position.
Figure 13:
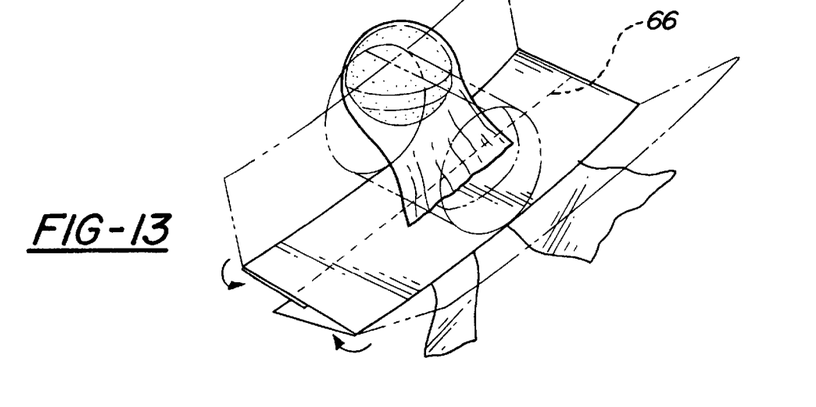
FIG. 13 is a perspective view of the embodiment of FIG. 12 in a folded position.

In still another embodiment of the present invention shown in FIGS. 12 and 13, if desired, the opening 46 provided in the embodiment of FIGS. 3 and 4 can be further sealed by providing a locking and sealing member 60 having foldable sides 62, 64 thereon that are on either side of an interior panel 66 having an opening 46' formed therein corresponding to the opening 46 in the embodiment of FIGS. 1–4.

In this embodiment, after the shield portion has been pulled through the locking and sealing member 60, the foldable edges 62, 64 are folded over into an overlapping relationship shown in FIG. 13 at broken line 66 that will cover the opening 46' to prevent leakage of fluid from the sponge when in its predeployment position.

Figure 15:
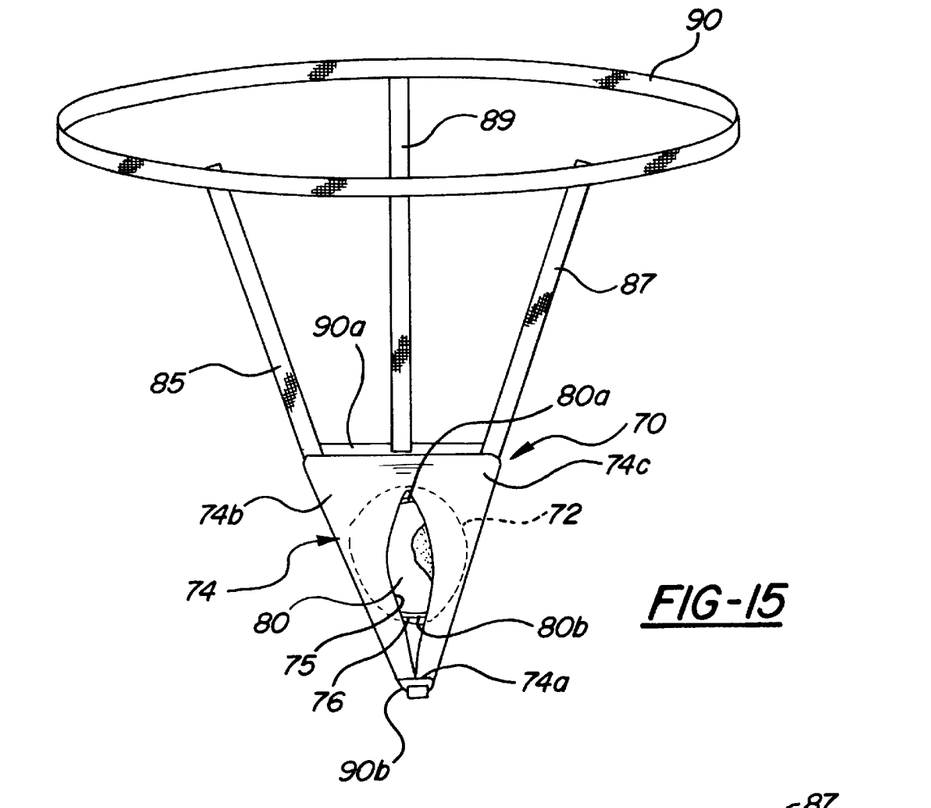
FIG. 15 is a front elevational view of still another embodiment of the present invention including a generally triangularly configured extension on the pouch of a female condom having a retention sponge therein; the extension adapted to be connected to straps for configuring the extension to cover the perineum of a user.
Figure 16:
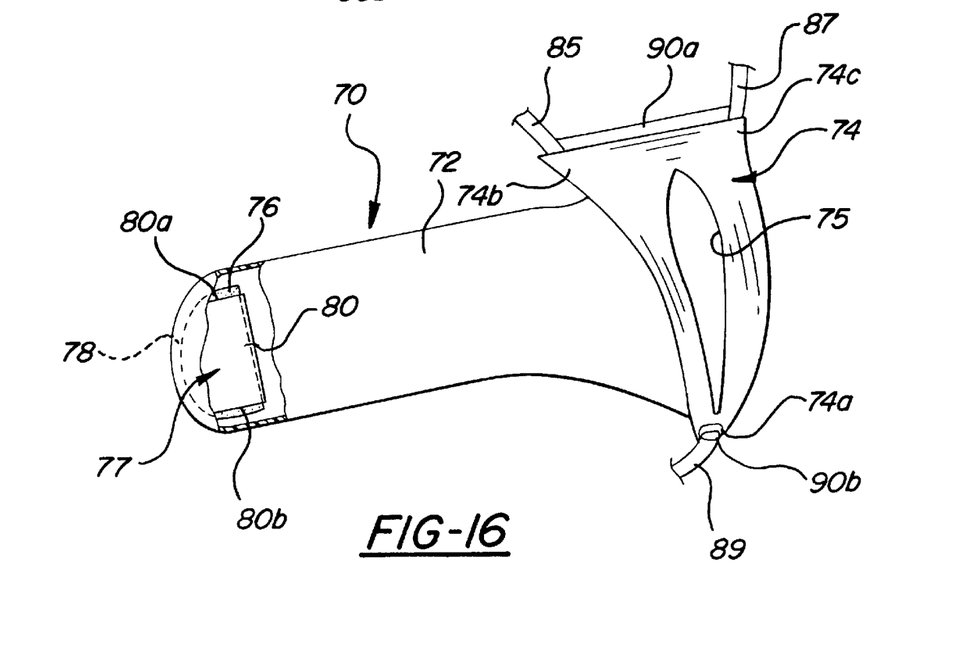
FIG. 16 is a perspective view of the embodiment of FIG. 15, partially broken away.
Figure 17:
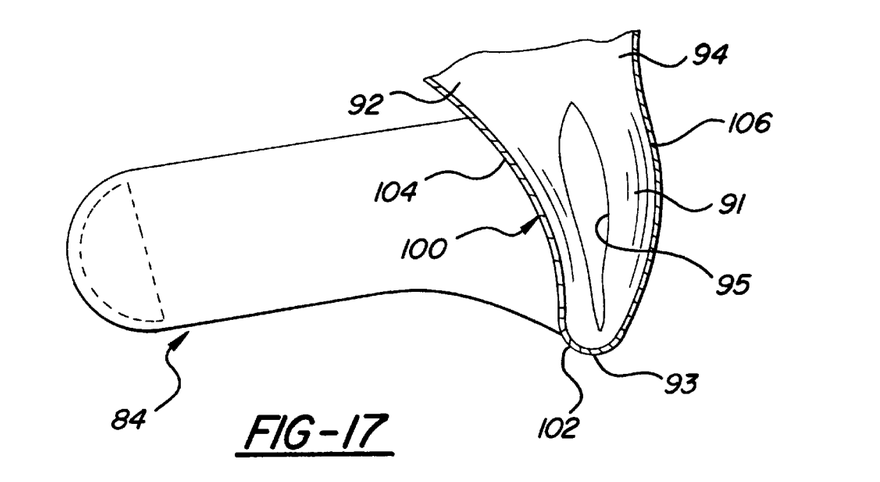
FIG. 17 is a perspective view of another embodiment of the invention including a wishbone member thereon for configuring extensions on a condom pouch to the perineum of a user.

In the embodiment of the invention shown in FIGS. 15 and 16, a female condom 70 is illustrated that includes a pouch 72 with an extension 74, having the same wall thickness as the pouch, e.g., for most materials in the range of 0.02 mm to 0.06 mm. The front extension 74 extensions has a triangular configuration of inverted isosceles shape with an apex 74a and a pair of wing segments 74b, 74c conformed to the general shape of the pelvic bone region and having a surface area that will cover the perineum of a user. The front extension 74 has the same wall thickness as pouch 72 throughout the planar extent of the surface area thereof for allowing unrestricted lateral contraction and expansion to accommodate body movement of the user. The extension 74 defines an opening 75 to the pouch interior and the opening 75 extends from the apex 74a of the inverted isosceles shape to the pair of wing segments 74b, 74c.

The retention sponge in this embodiment is shaped as a half moon sponge 76 connected by a strap 77 to the tip of a closed end 78 of the pouch 72. In this embodiment, the strap 76 is formed as a ring 80 having open sides 80a, 80b through which side portions 76a, 76b of the half moon shaped sponge extend. Antibiotics or spermicides can be added if desired. The half moon and ring type connection is applicable for use in the previously described embodiments, with it being understood that in such case the sponge would replace that shown in the first embodiment and the ring would replace the sponge retention pocket.

Figure 21:
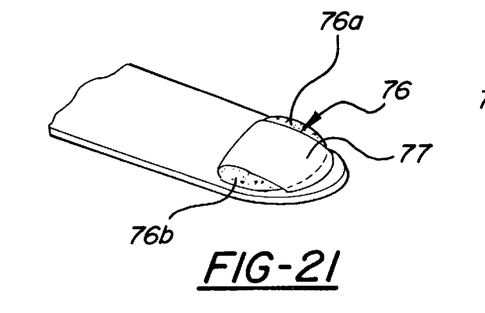
FIG. 21 is an enlarged fragmentary view of a retention member holding a retention sponge in place on the interior surface of condom pouch prior to formation of the telescoped predeployment position of FIG. 18.
Figure 22:
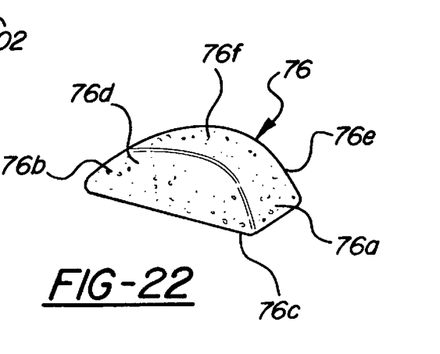
FIG. 22 is an enlarged perspective view of the retention sponge shown in the embodiments of FIGS. 15, 16 and FIGS. 17–20.

The half moon shaped sponge 76 and ring connector 77 are shown in FIG. 21 prior to being placed in a deployed position as shown in FIG. 16. The sponge 76 is shown in perspective in FIG. 22 as constituting one half of a circular disc that has a base 76c; side surfaces 76d and 76e; and a curved top 76f that has the side portions 76a, 76b at opposite ends thereof.

Figure 18:
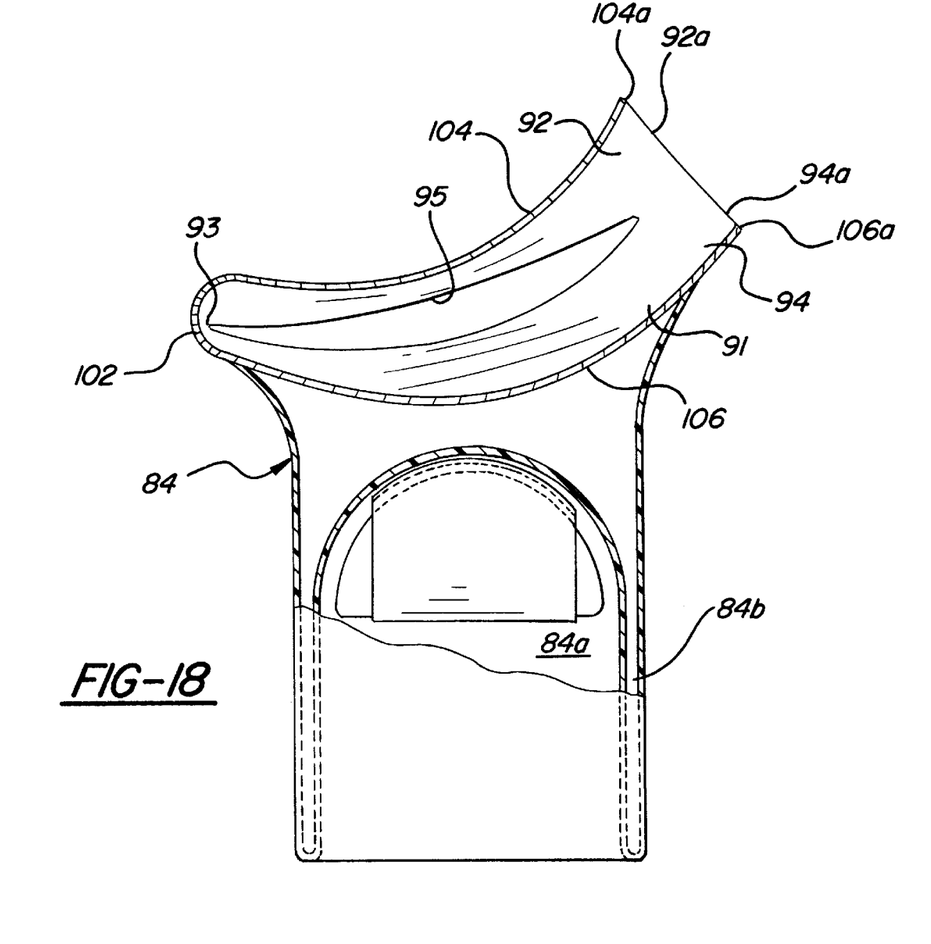
FIG. 18 is a view of the embodiment of FIG. 17 in a predeployment position in which the pouch is telescoped for ease of insertion of a retention sponge interiorly of a user.

As in the prior embodiments, prior to deployment, the pouch 72 is telescoped as shown at 82 in FIG. 18. In the predeployment position, the pouch 72 is located in front of the user and is held in place by two front straps 84, 86 and a rear strap 88 all joined at their distal ends by a waist band 90. Reinforcing strips 90a and 90b can be provided at the points of connection of straps to the extension 74.

All the prior embodiments have a locking and sealing member that will locate the sponge in a sealed relationship to the user in predeployment position. The locking and sealing mechanism will stop the spread of lubricant and keep the sponge in position, in a telescoped pouch.

If desired, the condom shown in the embodiments can be placed in a lubricated or spemicide containing package for providing desired lubrication when in use.

Referring now more specifically to the embodiment in FIGS. 17–20, the straps are omitted and a condom 84 when deployed is configured so that in itself will provide a self supporting adaptive configuration for covering the perineum without hindering lateral shifting movements of a user that will close and open the entrance to a pouch 86. More particularly, in this embodiment only a front extension 91 is provided. As in the embodiment of FIGS. 15–16, in this embodiment the front extension 91 has a triangular configuration of inverted isosceles shape with an apex 93 and a pair of wing segments 92, 94 conformed to the general shape of the pelvis region and having a surface area that will cover the perineum of a user. The front extension 91 has the same wall thickness as pouch 84 throughout the planar extent of the surface area thereof for allowing unrestricted lateral contraction and expansion to accommodate body movement of the user. Suitable wall thicknesses for most materials is in the range of 0.02 mm to 0.06 mm. The front extension defines an entrance 95 to the pouch formed between the two wing segments 92, 94. The wing segments 92, 94 are joined at the apex 93 and have free edges 92a, 94a thereon that are at a point spaced from the apex 93. Thus, when deployed the wing segments 92, 94 are integral extensions of the wall of the pouch 72 and define the entrance opening 95 to the pouch 72 that extends all the way to the apex 93 for ease of entry and for imparting unrestricted lateral movement to accommodate user movement. The entrance opening 95, itself is open at the top at a location that will be above the entrance to the pouch.

The use of integrally formed single wall thickness extensions on the pouch with free edges provides lateral freedom as in the case of the first embodiment in which the frontal shield is a single wall extension of the pouch.

A feature of the condom is the provision of a V-shaped spring member 100 that partially surrounds the wing portions 92, 94. In the broad aspect of the invention, the spring member is selected with an angle from anterior to posterior and side to side of user in order to conform to the perineal area of the user, in different positions, like walking, standing, sitting, prone position, etc.

More specifically, the V shaped spring member 100 includes an apex 102 that is located at the apex 93. Spaced outwardly diverging spring segments 104, 106 are joined at the apex 102. They each have a distal end 104a, 106a that extends to the wing edges 94a, 96a. The spring segments 104, 106 are lightly biased apart from one another to spread the wing portions 94, 96 to cover the perineum when the pouch 72 is in its deployed position. Since the wings are open at the edges 94a, 96a they will readily move laterally so that the spring segments can be moved toward one another if the user were to be seated following deployment of the condom. Such unrestricted configuration also enables the spring segments 104, 106 to be moved with respect to the apex 102 during use such that the distal ends 104a, 106a can almost close as shown in broken outline in FIG. 20 or can be fully separated to the width of the extended edges 94a, 96a as shown in solid line in FIG. 20. Such lateral contraction and extension provides adjustment of the shape of the extension 91 to the user during a wide range of movements, e.g., walking, sitting, stretching so that deployment of the condom will not be an undesirable distraction.

Figure 19:
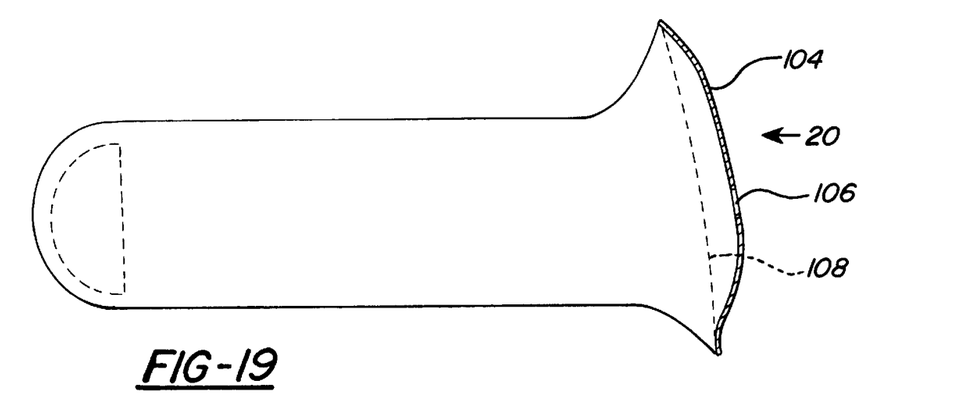
FIG. 19 is a side elevational view of the condom in FIG. 17 shown with the pouch extended in its deployed position and the entrance end disposed to cover the perineum of a user.
Figure 20:
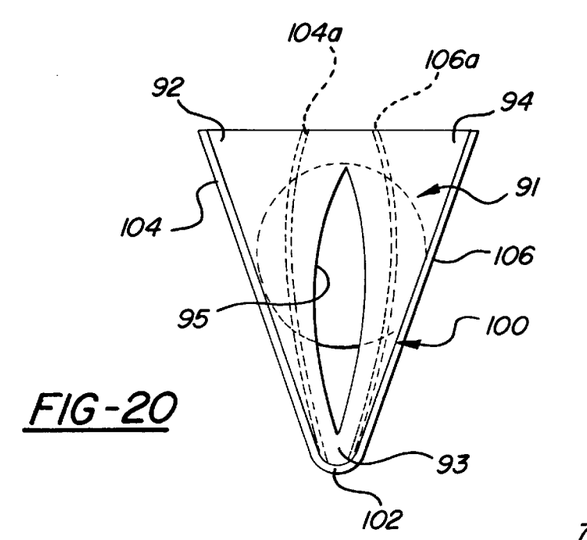
FIG. 20 is an end elevational view of the deployed condom looking in the direction of the arrow 20 in FIG. 19.

Additionally, as best shown in the side elevational view of FIG. 19, the spring segments 104, 106 each are bowed outwardly from the user such that inward pulling action will be absorbed by flattening of the spring segments 104, 106 as shown in dotted line at 108 in FIG. 19. Such action provides improved conformation to the perineum of a user since the spring segments 104, 106 are able to flex into the adjacent shape of a user in the vicinity of the pelvic bone while remaining free to laterally shift toward and apart from one another about the apex 102 that serves as a pivot point for lateral movement of the distal ends of the spring segments 104, 106.

The V-shaped spring design of FIGS. 17–20 will not contain a locking and sealing member because this design is packaged without any rolling. Also, in this design, the pouch will be telescoped. The telescope will contain a pocket in the front and a pocket in the back. Lubrication will be instilled in the pockets as shown at 84a and 84b in FIG. 18.

Figure 23:
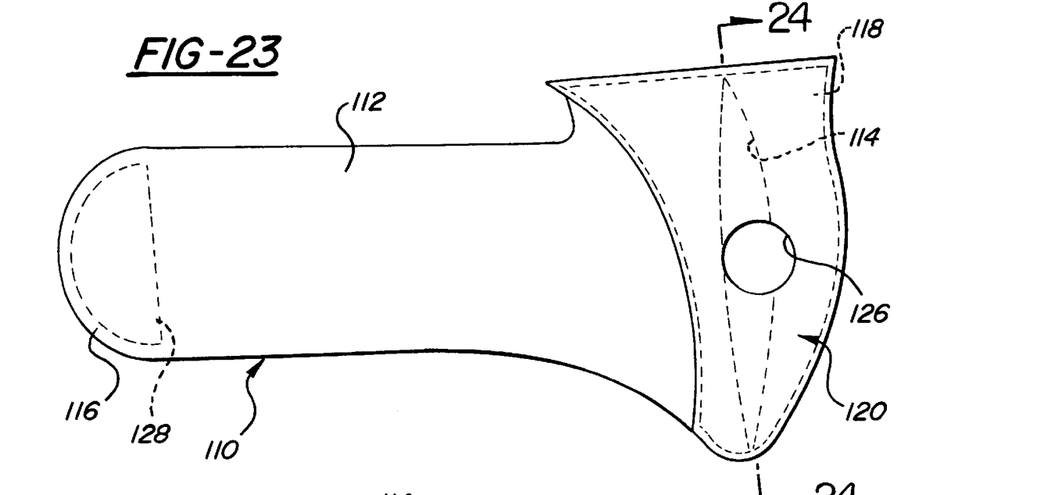
FIG. 23 is a perspective view of still another embodiment of the present invention.
Figure 24:
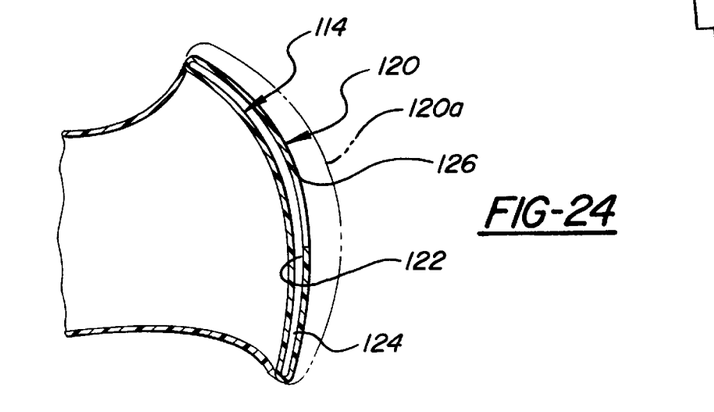
FIG. 24 is a sectional view taken along the line 24—24 of FIG. 23 looking in the direction of the arrows.

In still another embodiment of the invention shown in FIG. 23, a female condom 110 is shown having a pouch 112 with an entrance 114 and a closed end 116. In this embodiment the entrance has a double wing configuration on the material that extends from the pouch and has the same frontal appearance as the material forming the entrance to the condom shown in FIGS. 15–19. In this embodiment the V-shaped spring 102 is omitted and it is replaced by a preformed layer cover 120 with a shape conformed to the double wing surface 118. The preformed layer can be formed of a suitable thermoplastic material that can be vacuum formed or otherwise molded into a shape that will include an inner surface 122 that generally conforms to the perineum of a user at the pelvis bone and that will flex to conform thereto. Additionally, the cover 120 forms a two layer entrance having a space 124 therebetween that defines a labyrinth seal for preventing leakage from interiorly of the pouch to the exterior of the two layer entrance. A further feature is that the cover 120 includes an opening 126 generally aligned with the interior of the pouch and adapted to form a pilot opening for directing an erect penis through the two layer entrance into the interior of the pouch. The cover 120 further will be freely moveable outwardly of the wing surface 118 material to provide an extension on the end of the pouch to prevent inadvertent withdrawal during coitus. The cover 120 is shown in solid line two layer piloting configuration in FIG. 23 and is shown in an extension position at dotted line position 120a in FIG. 23.

A retention sponge 128 is provided that can have either the open, ring type connection strap or can have a closed pocket type strap for holding it on the inside end surface of the pouch 112.

Figure 25:
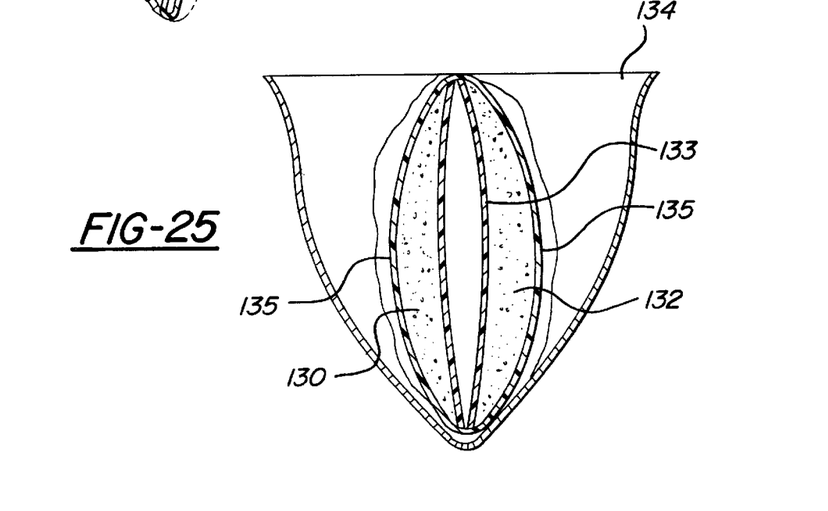
FIG. 25 is an end elevational view of still another embodiment of the present invention partially broken away to show outwardly disposed cavity fillers.
Figure 26:
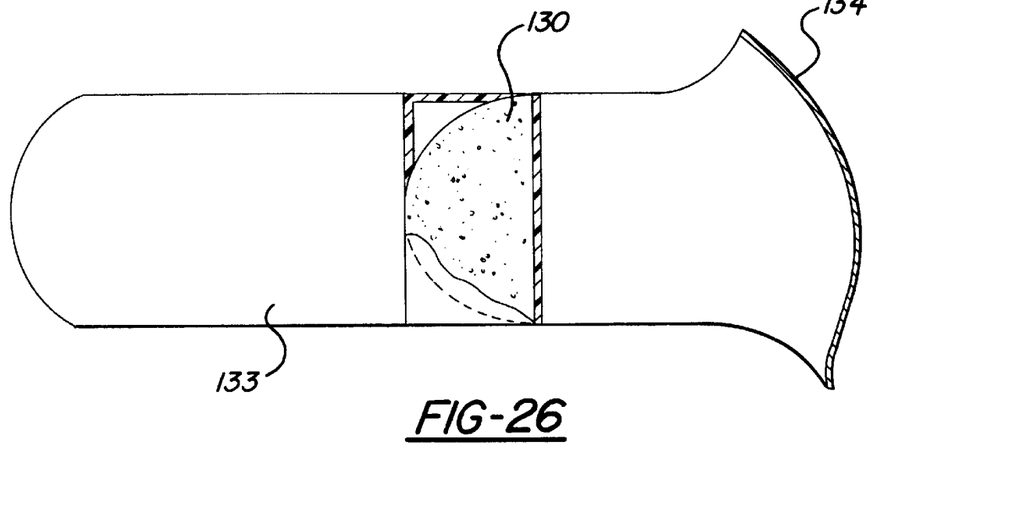
FIG. 26 is a side elevational view of the embodiment in FIG. 25 showing the pouch in a predeployment telescoped position.
Figure 27:
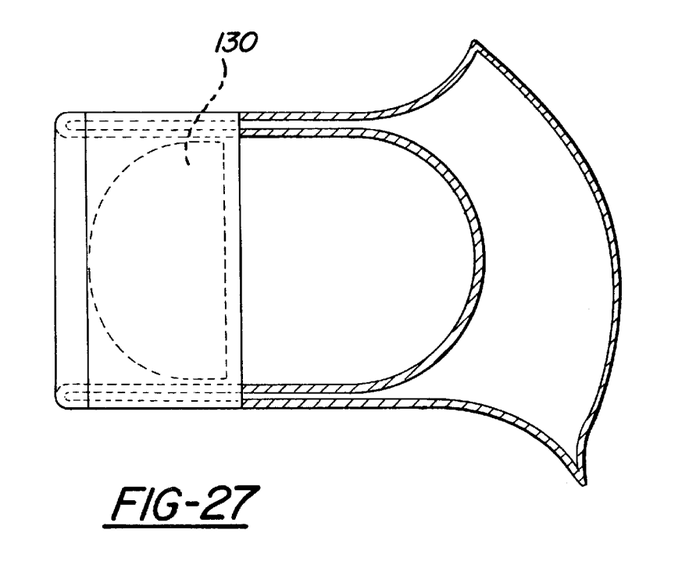
FIG. 27 is a side elevational view of the embodiment in FIG. 25 shown in a fully deployed position.

In the embodiment of the invention shown in FIGS. 25–27 a pair of additional sponge like members cavity filler members 130 and 132 are connected to a pouch 133 spaced from an entrance extension 134 like those previously described. Each of the filler members 130, 132 is made of sponge like material as in the previous sponge elements. They are each located in pockets 135 formed on the outside of the pouch 133 on either side thereof. The retention sponge on the closed end of the pouch can be eliminated. The cavity filler members have a thickness at their center of about one to one and one-half cm. They taper in the direction of the closed end to about a thickness of onehalf cm. The members 130, 132 are provided to fill the inside of vaginal cavity that has been extended because of childbirth or the like. The members 130, 132 are located so as to fill the anterior one-third of the vagina cavity and cause tightness around the glans penis. Consequently, the female condom is configured to provide sexual stimulation concurrently to both female and male members.

Figure 28:
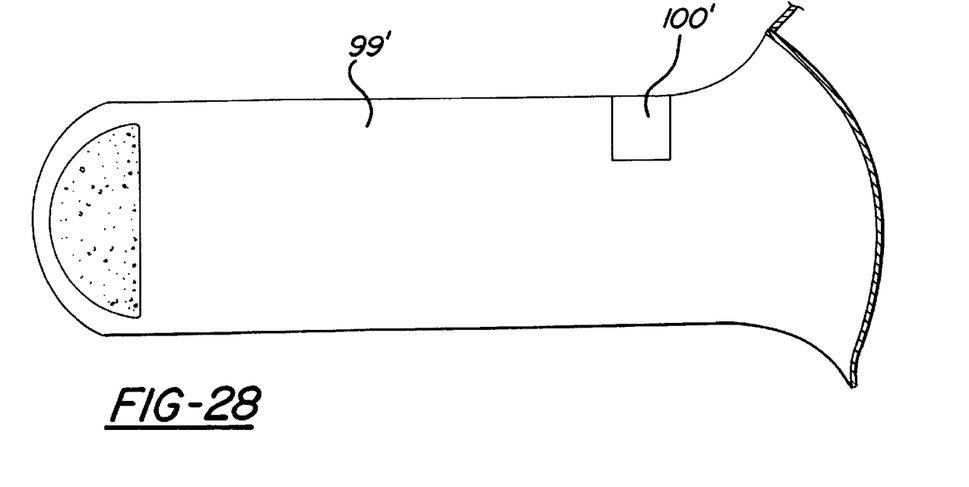
FIG. 28 is a side elevational view of still another embodiment of the invention.

In the embodiment shown in FIG. 28, an elevated, semi-hard patch 100 is incorporated on the pouch 99 near the open end, at the upper surface thereof, in order to cause stimulation of the clitoris during intercourse.

Figure 29:
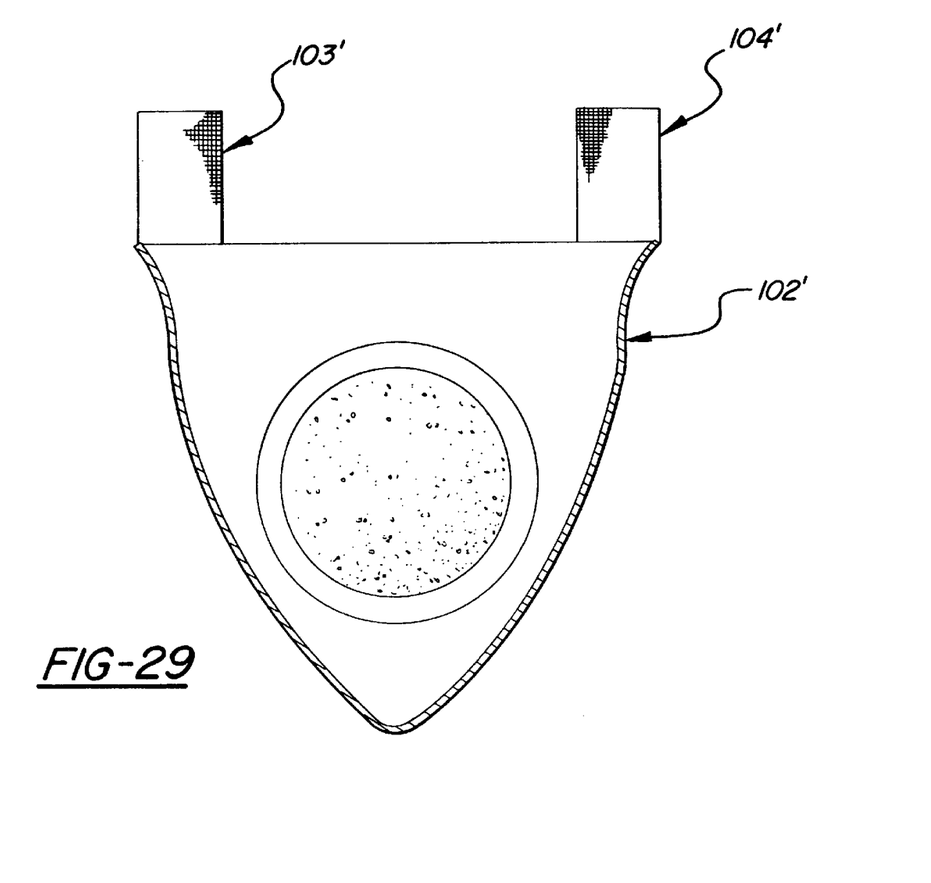
FIG. 29 is an end elevational view of the open end of the embodiment in FIG. 28.

In the embodiment shown in FIG. 29, the outer most portion of the open end of the pouch near the rim 102 is provided with two adhesive bands 103, 104 to be applied to the abdomen after deployment of the condom to prevent drooping of the rim.

In the present invention, the female condom can be formed of material preferably made of elastic impermeable substances such as natural rubber (e.g., latex), synthetic rubber (e.g., silicone rubber), or polyurethane. Other useful materials include non-elastic substances such as various thermoplastic materials including polyethylene.

The retention sponge shown in the various embodiments of the invention can be formed of a resilient, porous material such as natural sponge material or a suitable, soft, porous sponge-like natural or synthetic material having voids. Suitable materials include natural sponge material; soft rubber open lattice material; polyurethane foam of the open cell blown type and the like that can be compressed into a compact shape and that are resiliently expandable into a retention position when deployed. The voids can be impregnated with lubricant, spermicides, fungicides, bactericides or antiviral agents that can be slowly released therefrom to protect a user as desired.

While the best mode for carrying out the invention has herein been described in detail, those familiar with the art to which this invention relates will recognize various alternative designs and embodiments for practicing the invention.

What is claimed is:

1. A female condom having a pouch with a closed end and a tubular portion insertable into a vagina and the pouch further including an open end thereon connected to a shield portion secured to the pouch and wherein the shield portion has an outer surface and an inner surface for covering the perineum of a user and having a retention sponge within the pouch characterized by:

said pouch having an extension thereon forming a perineal shield having the same wall thickness as the pouch and is configured to laterally collapse and laterally expand freely to accommodate body movements of a user;

said pouch having a predeployment position on the outer surface of said shield portion and a deployed position on the inner surface portion of said shield portion;

said pouch including a telescoped portion in its predeployment position defining an exteriorly accessible pocket; and a retention sponge located within said exteriorly accessible pocket.

2. The female condom of claim 1 further characterized by:

a locking and sealing member covering said pocket for sealing said retention sponge when in said exteriorly accessible pocket;

said locking and sealing member further including a segment thereon connected to said pouch adjacent said open end thereof for locking said telescoped portion in its predeployment position;

said locking and sealing member being removable from said telescoped portion for deployment thereof;

said telescoped portion insertable with said retention sponge from the outer surface of said shield portion through said open end of said pouch into a deployed position wherein said retention sponge is located interiorly of a user against said closed end for preventing pull-out during use.

3. The female condom of claim 2 further characterized by said locking and sealing member fluidly seals said retention sponge within said pocket.

4. The female condom of claim 2 further characterized by said locking and sealing member being a cover formed as a patch; said patch removably connected to said pouch.

5. The female condom of claim 2 wherein said locking and sealing member includes an opening therein through which said shield portion extends outwardly from said pouch for clamping said shield portion at said telescoped portion prior to deployment.

6. The female condom of claim 2 further characterized by said locking member and seal member being a ring member having an opening therein through which said shield portion is located prior to deployment of the female condom.

7. The female condom of claim 2 wherein said locking and sealing member includes first and second ends thereon joined together adjacent said outer surface of said shield portion and in the proximity of said open end of said pouch.

8. The female condom of claim 7 further characterized by said locking and sealing member including an opening therein through which said shield portion extends outwardly from said pouch for clamping said shield portion at said telescoped portion prior to deployment.

9. The female condom as in one of claims 5, 6 or 8 further characterized by said locking and sealing member having foldable sides for closing said opening following connection of said locking and sealing member on said pouch.

10. The female condom of claim 1 further characterized by said pouch having a retainer member for holding said retention sponge on said pouch adjacent said closed end thereof.

11. The female condom of claim 10 further characterized by said retainer member being a pocket closed in the direction of said open end of said pouch.

12. The female condom of claim 10 further characterized by said retainer member formed as a strap connected across the width of said closed end of said pouch for forming opposite open passages for absorption of semen after ejaculation.

13. The female condom of claim 10 further characterized by said sponge being medicated by spermicide.

14. The female condom of claim 10 further characterized by said retainer member formed as a pocket having side openings therein.

15. The female condom of claim 1 further characterized by said shield portion having an open-ended, V-shaped spring member with characteristics of a spring mechanism to conform to the pelvis of the user.

16. A female condom of claim 15 further characterized by incorporation of spring action of the V-shaped spring member with an angle from anterior to posterior and side to side of user in order to conform to the perineal area of user, in different positions, like walking, standing, sitting, prone position, etc.

17. A female condom of claim 15 further characterized by said open end covered by an attached sealed shield with a small opening to allow passage of the penis during intercourse.

18. A female condom of claim 15 further characterized by adhesive attachments at the upper end of the pouch for attachment to the abdomen of the user to prevent drooping of said V shaped spring member.

19. The female condom of claim 1 wherein said shield portion has extensions that have a triangular configuration of inverted isosceles shape conformed to the pelvic bone of a user and having the same wall thickness as said pouch throughout the planar extent of said extensions for allowing unrestricted lateral contraction and expansion and wherein an opening is provided in said extensions; said opening extending to said apex of said inverted isosceles shape and to a pair of wing portions on said triangular configuration.

20. A female condom of claim 19 further characterized by two separate sponge members incorporated on both sides separately and exteriorly near the open end of the pouch to prevent pouch pullout during intercourse.

21. A female condom of claim 20 further characterized by a telescoping closed end for deployment of the condom into the vagina.

22. A female condom of claim 1 having elastic straps; said front and back portions of the shield are placed with said elastic straps.

23. A female condom of claim 22 said shield terminating in a thicker and comparatively non-elastic member incorporated in said ends of the shield to hold elastic straps.

24. A female condom of claim 1 wherein said condom has another shield; said perineal shield is covered by said another shield completely; a small opening in said another shield to allow passage of a penis during intercourse.

25. A female condom of claim 24 wherein said perineal shield is freely movable with an erect penis without dislodging it during intercourse.

26. A female condom of claim 24 wherein said another covering shield over said perineal shield is sealed to the periphery of said perineal shield to prevent penile secretions from spilling out of the female condom.

27. A female condom of claim 1 further characterized by two separate sponge members incorporated on both sides separately and exteriorly near the open end of the pouch to prevent pouch pullout during intercourse.

28. A female condom of claim 27 further characterized by a telescoping closed end for deployment of the condom into the vagina.

29. A female condom of claim 1 further characterized by a raised patch of material located near the open end of the pouch exteriorly behind the shield for stimulation of the clitoris.

30. A female condom of claim 1 wherein said clitoral stimulation device is attached to the exterior or interior side near the open end of the pouch.

31. A female condom of claim 30 wherein said clitoral device is a raised surface portion on said pouch.

32. A female condom of claim 30 wherein said clitoral device is an integrally molded part of said pouch.

33. A female condom of claim 30 wherein said clitoral device is a circular patch.

* * * * *